United States Patent
Andreevich et al.

(10) Patent No.: US 8,362,167 B2
(45) Date of Patent: Jan. 29, 2013

(54) FLUORINATED IMIDOYLAMIDINE VULCANIZING AGENTS FOR CURING PERFLUOROELASTOMERS POLYMERS

(75) Inventors: Gubanov Viktor Andreevich, Saint-Petersburg (RU); Kollar Alexander Nikolaevich, Saint-Petersburg (RU); Volkova Margarita Alekseevna, Saint-Petersburg (RU); Tsipkina Irina Mikhailovna, Saint-Petersburg (RU)

(73) Assignee: LODESTAR Inc., Howell, NJ (US)

( * ) Notice: Subject to any disclaimer, the term of this patent is extended or adjusted under 35 U.S.C. 154(b) by 0 days.

(21) Appl. No.: 11/822,829

(22) Filed: Jul. 10, 2007

(65) Prior Publication Data

US 2008/0035883 A1 Feb. 14, 2008

(51) Int. Cl.
C08F 14/18 (2006.01)
C08F 14/26 (2006.01)

(52) U.S. Cl. .................. 526/248; 525/326.1; 525/326.2; 525/326.3; 525/326.4; 525/359.1; 525/359.3; 525/374; 525/379; 525/381; 525/389; 526/242; 526/247; 526/250; 526/253; 526/254; 526/255; 526/291; 526/292.8; 526/294; 526/297; 526/298; 528/401; 528/422; 528/425; 564/225; 564/243

(58) Field of Classification Search ............... 525/326.1, 525/326.2, 326.3, 326.4, 359.1, 359.3, 374, 525/379, 381, 389; 526/242, 247, 248, 250, 526/253, 254, 255, 291, 292.8, 294, 297, 526/298; 528/401, 422, 425; 564/225, 243
See application file for complete search history.

(56) References Cited

U.S. PATENT DOCUMENTS

| | | | | |
|---|---|---|---|---|
| 3,734,976 A | * | 5/1973 | Dorfman et al. | 525/418 |
| 4,557,869 A | * | 12/1985 | Paciorek et al. | 552/3 |
| 5,498,657 A | * | 3/1996 | Sugiyama et al. | 524/463 |
| 5,637,648 A | * | 6/1997 | Saito et al. | 525/326.3 |
| 5,767,204 A | * | 6/1998 | Iwa et al. | 525/359.3 |
| 6,638,999 B2 | * | 10/2003 | Bish et al. | 524/195 |
| 2006/0287438 A1 | * | 12/2006 | Mansfield et al. | 525/326.2 |
| 2007/0027260 A1 | * | 2/2007 | Aufdermarsh et al. | 525/199 |

OTHER PUBLICATIONS

Croft, T. S., Zollinger, J. L. Ind. & Eng. Chem. Prod. Res. Develop. 1974, 13(2), 144-147.*
Logothetis, A. L. Prog. Polym. Sci. 1989, 14(2), 251-296.*
CAS Abstract of: "Exchange reactions of N'-(perfluoroacylimidoyl)perfluoroalkylamidines with perfluorocarboxylic acid nitriles", Davtyan, M. et al, Izvestiya Akademii Nauk SSSR, Seriya Khimicheskaya (1980), (6), 1414-1415.*
Davtyan, M. M. et al. "Exchange reactions of N'-(perfluoroacylimidoyl)perfluoroalkylamidines with perfluorocarboxylic acid nitriles". Izvestiya Akademii Nauk SSSR, Seriya Khimicheskaya 1980, 6, 1414-1415.*
Davtyan, M. M. et al. "Cyclotrimerization of perfluorocarboxylic acid nitriles and their cotrimerization with benzonitrile". Izvestiya Akademii Nauk SSSR, Seriya Khimicheskaya 1980, 2, 425-428.*
Tolmacheva, G. M. et al. "Acylation-dehydration of N'-(perfluoroacylimidoyl)perfluoroalkylamidines with carboxylic and polyfluoro- and perfluorocarboxylic acid anhydrides". Izvestiya Akademii Nauk SSSR, Seriya Khimicheskaya 1979, 3, 580-585.*
Redina, T. N. et al. "Cocyclotrimerization of mono- and dinitriles of perfluorocarboxylic acids under high pressure". Izvestiya Akademii Nauk, Seriya Khimicheskaya 1995, 9, 1814-1816.*

* cited by examiner

Primary Examiner — Richard A Huhn
(74) Attorney, Agent, or Firm — Isaac A. Angres

(57) ABSTRACT

The invention provides a compound and tautomeric forms thereof having the formula:

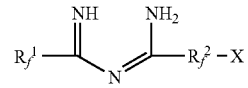

wherein $R_f^1$ is selected from the group consisting of hydrogen, a straight chain, branched secondary or branched tertiary $C_1$-$C_{20}$ perfluoroalkyl group optionally containing ether or thioether linkages and $C_1$-$C_{10}$ perfluoroalicyclic group optionally containing ether or thioether groups; $R_f^2$ is a straight or branched $C_1$-$C_{20}$ perfluoroalkylene group optionally substituted with ether and thiother linkages; and X is selected from the group consisting of fluorine and

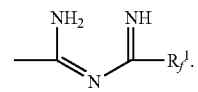

The invention also provides perfluoroelastomeric compositions cured with the perfluoroimidoylamidines of the invention as well as combinations of perfluoroimidoylamidines and other curing agents.

13 Claims, No Drawings

FLUORINATED IMIDOYLAMIDINE VULCANIZING AGENTS FOR CURING PERFLUOROELASTOMERS POLYMERS

This application claims the priority benefit under 35 U.S.C. section 119 of Russian Patent Application No. 2006124713 entitled "Compositions based on copolymers of Tetrafluoroethylene and Perfluoroalkyl Vinyl Ethers" filed Jul. 10, 2006, which is in its entirety herein incorporated by reference.

FIELD OF INVENTION

This invention relates to novel fluorinated imidoylamidines useful as curing agents. The present invention also relates to a curative composition as well as curable and cured fluoropolymer compositions, methods of making fluoropolymer compositions, and fluoro-polymer articles.

The invention further relates to curable perfluoroelastomer compositions which exhibit a rapid cure rate and which, when cured, have outstanding thermal stability and chemical resistance.

The instant invention also pertains to making rubber blends based on perfluorinated copolymers, containing functional groups, particularly copolymers of tetrafluoroethylene (TFE), perfluoroalkyl vinyl ethers (PAVE) and perfluoroalkyl vinyl ethers containing a nitrile group.

The present invention also pertains to processes of preparing perfluoroelastomeric compositions containing fluorinated imidoylamidines as curing agents.

The present invention also provides perfluoroelastomer compositions which are designed for application in the chemical, oil and gas industry, electronic components production, and other areas requiring high thermo-aggressive resistant properties.

The instant invention also relates to perfluoroelastomeric compositions, which when cured have light color, good physical and mechanical properties, increased thermal stability under stress condition (i.e., when stretched) and are stable in aggressive chemical environments.

BACKGROUND OF THE INVENTION

Perfluoroelastomers (elastomeric perfluoropolymers) are polymeric materials which exhibit outstanding high chemical resistance and temperature tolerance and accordingly are particularly adapted for many industrial uses in which elevated temperatures and/or corrosive chemicals are encountered. The outstanding properties of perfluoropolymers are largely attributable to the stability and inertness of the copolymerized perfluorinated monomer units which make up the major portion of the polymer backbone, e.g., tetrafluoroethylene and perfluoro(alkyl vinyl)ethers. In order to achieve good elastomeric properties, the perfluoropolymers must be crosslinked. To this end, a small percentage of a monomer having a functional group is copolymerized with the perfluorinated monomer units. Monomers containing nitrile functional groups, such as perfluoro-8-cyano-5-methyl-3,6-dioxa-1-octene, are especially preferred. Such compositions are described in U.S. Pat. Nos. 4,281,092 and 4,394,489; and in International Application WO 95/22575.

The fluorinated polymers and particularly perfluorinated elastomers have unique thermal and chemical resistance properties. Preparation of these fluoroelastomers from fluoropolymer precursors (sometimes referred to as "raw gums" or "gum"), however, can be difficult. The fluoropolymer precursors and compositions containing the fluoropolymer precursors may be incompatible with processing and curing additives. In addition to incompatibility, certain curing additives are disposed to undesirable homopolymerization, which can lead to processing difficulties in preparing fluorinated elastomers.

The cured or cross-linked fluoroelastomers are tolerant to high temperatures and aggressive chemical environments and therefore are particularly useful as seals, gaskets, and molded parts in systems that are exposed to elevated temperatures and/or corrosive materials. For sealing applications that require resistance to the most extreme conditions, perfluorinated elastomers are used. Such parts are used in applications such as automotive, chemical processing, semiconductor, aerospace, and petroleum industries, among others.

In order to fully develop physical properties such as tensile strength, elongation, and compression set, elastomers must be cured, i.e. crosslinked. In the case of fluoroelastomers, this is generally accomplished by mixing uncured polymer (i.e. fluoroelastomer gum) with a polyfunctional curing agent and heating the resultant mixture under pressure, thereby promoting chemical reaction of the curing agent with active sites along the polymer backbone or side chains. Interchain linkages produced as a result of these chemical reactions cause formation of a crosslinked polymer composition having a three-dimensional network structure. Commonly used curing agents for fluoroelastomers include difunctional nucleophilic reactants, such as polyhydroxy compounds. Alternatively, peroxidic curing systems containing organic peroxides and unsaturated coagents, such as polyfunctional isocyanurates, may be employed.

Many fluoroelastomers often include a functional group to facilitate cure in the presence of a curative or catalyst. One class of useful functional group used in perfluoroelastomers includes nitrile group-containing monomers, for which organotin catalysts have been used as curing components. However, such catalysts can leave undesirable extractable metal residues in the cured product and are undesirable for environmental reasons. Ammonia-generating compounds have also been used as a cure system component in fluoroelastomers, but these cure systems lack the desired level of rheological control during processing. In addition, most known fluoroelastomers are cured into colored or opaque materials. A few fluoroelastomers or perfluoroelastomers have been described as colorless and/or transparent, yet can be cloudy or milky in appearance, and have rather high compression set when made into seals, even when measured at relatively low temperatures (up to 200° C.).

Copolymers containing 50-75 Mole % of TFE links, 49.8-25.0% of PAVE links and 0.2-5 Mole % of perfluoroalkyl vinyl ether links having the following chemical structures, have been described in U.S. Pat. No. 5,565,512:

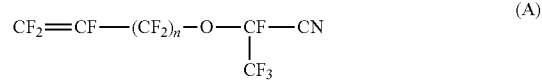
(A)

where n is 2 to 4, or

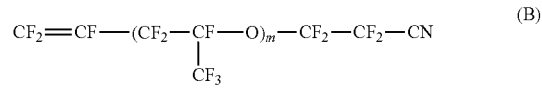
(B)

where m is 0 to 4.

The above perfluoroelastomer compositions include an ammonium salt of an organic or inorganic acid as a curing agent. The content of the curing agent is 0.2 to 5 parts by weight per 100 parts by weight parts of the perfluoroelastomer. The above compositions can include a filler (for example, Carbon Black), pigments, plasticizers and other special fillers.

Cured formulations of the above composition have high strength of around 17.8-22.2 Mpa, light gray color or transparent if not filled with Carbon Black. The above compositions have poor thermal resistance in stress conditions. Even at 200° C. for 70 hours the compression set is 37-49%. Also they are not stable to strong nitric acid (swelling in 60% $HNO_3$ for 70 hours at 80° C. is +0.7).

U.S. patent application No. 2002/0061977 copolymer compositions containing 62% TFE, 36.8 mole % PAVE and 1.2 mole % perfluorovinyl ether of structure A or B (as shown above), including 0.05-10 weight parts of a curing agent of the structure $R'C(OR)_2=NH$ and its salts, where R' and R are alkyl, aryl, aralkyl, alkenyl per 100 parst by weight of copolymer. The composition can also contain carbon, fluoropolymer fillers, plasticizers and other additives. Vulcanized compositions without carbon or colorant have no significant color change and have good physical and mechanical properties. According to the authors of this patent application compression set at 300° C. for 22 hours is 15.3%, but at 330° C. for 24 hours is 50-60%. Additionally, the strength of the unfilled vulcanized compositions is 5 to 9 Mpa.

Russian Patent No. 2,137,781 describes perfluoroelastomeric compositions based on a copolymer containing 42-70 mole % of TFE links, 25-55 mole % PAVE links, 1-4 mole % perfluorovinyl ether of structure A or B, also include 1 part by weight per 100 parts by weight parts of the copolymer, of 4,4'-[2,2,2-trifluoro-1-(trifluoromethyl)-ethyl-idene]bis(2-aminophenol) (CAS registry number 83558-87-6) referred to as BOAP in this patent as a curing agent. The composition can also contain a filler, for example, carbon black. Vulcanized compositions based on the above copolymer are well processed on conventional equipment and have good physical and mechanical properties. The disadvantage of such composition is visible color even in the unfilled state. According to the authors of the patent, compression set at 275° C. for 24 hours is 12-15% and at 300° C. is 26-51%. Also, the above compositions have poor thermal stability under stress conditions and poor stability in strong nitric acid.

Accordingly, there remains a need in the art for improved curing agents capable of more easily dispersing in and more quickly curing perfluoroelastomers, particularly cyano curable perfluoroelastomers. There is further a need in the art for a cure accelerator for perfluoroelastomer curatives which accelerate the cure rate of and maintain the beneficial properties of perfluoroelastomers. The shortcomings of the prior art agents noted above may be overcome by employing derivatives thereof in accordance with the present invention.

OBJECTS OF THE INVENTION

It is a first object of the present invention to provide novel fluorinated imidoylamidines.

It is another object of the invention to provide novel fluorinated imidoylamidines useful as curing agents.

A further object of the invention is to provide novel perfluoroelastomeric compositions cured with fluorinated imidoylamidines.

A still further object of the invention is to provide novel perfluoroelastomeric compositions, which when cured have light color, increased thermal stability under stress condition and are stable in aggressive media for example strong nitric acid.

An additional object of the invention is to provide novel perfluoroelastomeric compositions, which when cured have good physical and mechanical properties.

An additional object of the present invention is novel perfluoroelastomeric compositions, which when cured have increased thermal stability.

Still, another object of the invention is to provide perfluoroelastomeric compositions, which when cured are stable to strong nitric acid.

Another important object of the invention is to provide perfluoroelastomer compositions which exhibit a rapid cure rate and which, when cured, have outstanding thermal stability and chemical resistance.

These and other objects of the present invention will more readily become apparent from the description and examples which follow.

SUMMARY OF THE INVENTION

The present invention provides a compound having the formula I and tautomeric forms thereof:

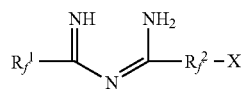

wherein $R_f^1$ is selected from the group consisting of hydrogen, a straight chain, branched secondary or branched tertiary $C_1$-$C_{20}$ perfluoroalkyl group optionally containing ether or thioether linkages and $C_1$-$C_{10}$ perfluoroalicyclic group optionally containing ether or thioether groups; $R_f^2$ is a straight or branched $C_1$-$C_{20}$ perfluoroalkylene group optionally substituted with ether and thiother linkages; and X is selected from the group consisting of fluorine and

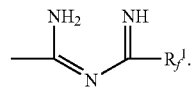

The invention further provides compounds and tautomeric forms thereof of the formula:

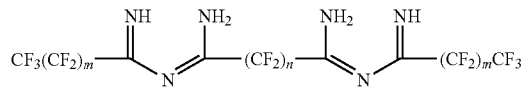

wherein n=1-8 and m=0-7. In this patent compounds of this general structure (see above) are referred to as DPIA (perfluoro diimidoylamidines)

The instant invention also provides a compound and tautomeric forms having the formula

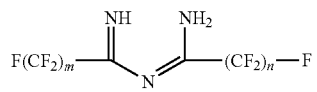

wherein n=1-8 and m=0-7. In this patent compounds of this general structure are referred to as PIA (perfluoro imidoylamidines)

The invention is also directed to a composition comprising: (a) a fluorocarbon polymer; and (b) a curing agent selected from the group consisting of a fluorinated imidoylamidine and a fluorinated diimidoylamidine and mixtures thereof.

Additionally, the invention provides a curable perfluoroelastomer composition comprising: (a) a perfluoroelastomer comprising copolymerized units of (1) a perfluoroolefin; (2) a perfluorovinyl ether selected from the group consisting of perfluoro(alkyl vinyl)ethers, perfluoro(alkoxy vinyl)ethers, and mixtures thereof; and (3) a functional group containing monomer having at least one nitrile group, selected from the group consisting of fluorinated olefins having at least one nitrile group, fluorinated vinyl ethers having at least one nitrile group, and mixtures thereof; and (b) about 0.1 to about 10 parts by weight per hundred parts by weight perfluoroelastomer of a fluorinated imidoylamidine curing agent.

The invention also provides a curing composition comprising:

(a) 0.1% to 99.9% by weight of a compound of the formula I and tautomeric forms thereof:

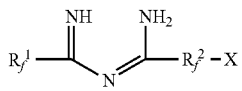

I wherein $R_f^1$ is selected from the group consisting of hydrogen, a straight chain, branched secondary or branched tertiary $C_1$-$C_{20}$ perfluoroalkyl group optionally containing ether or thioether linkages and $C_1$-$C_{10}$ perfluoroalicyclic group optionally containing ether or thioether groups; $R_f^2$ is a straight or branched $C_1$-$C_{20}$ perfluoroalkylene group optionally substituted with ether and thiother linkages; and X is selected from the group consisting of fluorine and

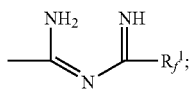

and
(b) 0.1% to 99.9% by weight of a compound of the formula:

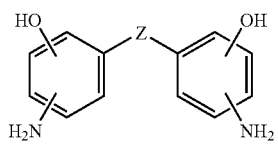

wherein Z is $SO_2$, O, CO, alkyl of 1-6 carbon atoms, perfluoroalkyl of 1-10 carbon atoms, or a carbon-carbon bond linking the two aromatic rings.

Furthermore, the instant invention also provides perfluoroelastomeric compositions cured with a composition comprising: (a) 0.1% to 99.9% by weight of a compound of the formula I and tautomeric forms thereof:

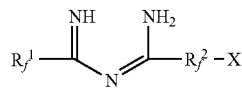

I wherein $R_f^1$ is selected from the group consisting of hydrogen, a straight chain, branched secondary or branched tertiary $C_1$-$C_{20}$ perfluoroalkyl group optionally containing ether or thioether linkages and $C_1$-$C_{10}$ perfluoroalicyclic group optionally containing ether or thioether groups; $R_f^2$ is a straight or branched $C_1$-$C_{20}$ perfluoroalkylene group optionally substituted with ether and thiother linkages; and X is selected from the group consisting of fluorine and

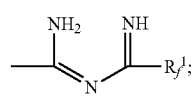

and
(b) 0.1% to 99.9% by weight of a compound of the formula:

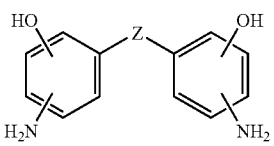

wherein Z is $SO_2$, O, CO, alkyl of 1-6 carbon atoms, perfluoroalkyl of 1-10 carbon atoms, or a carbon-carbon bond linking the two aromatic rings.

DESCRIPTION OF THE PREFERRED EMBODIMENTS

The present invention relates to compounds and tautomeric forms thereof of the formula:

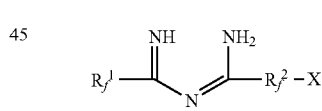

I wherein $R_f^1$ is selected from the group consisting of hydrogen, a straight chain, branched secondary or branched tertiary $C_1$-$C_{20}$ perfluoroalkyl group optionally containing ether or thioether linkages and $C_1$-$C_{10}$ perfluoroalicyclic group optionally containing ether or thioether groups; $R_f^2$ is a straight or branched $C_1$-$C_{20}$ perfluoroalkylene group optionally substituted with ether and thiother linkages; and X is selected from the group consisting of fluorine and

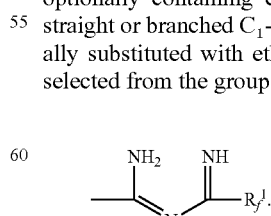

Compounds and tautomeric forms thereof that are particularly preferred in the present invention are those having the formula

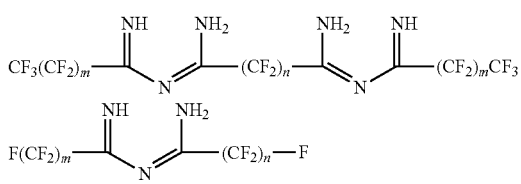

wherein n=1-8 and m=0-7.

The perfluoroimidoylamidines of the invention were synthesized by addition of 2 mol perfluoromonoamidines to 1 mol of perfluorodinitrile as described T. S. Zollinger, J. 1. *Ind. & Eng. Chem. Prod. Res. Develop.* 1974, 13(2), 144-147.

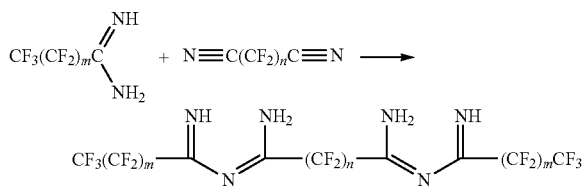

wherein (n=1-8, m=0-7).

The corresponding intermediates used in making the perfluoroimidoylamidines of the invention are made as follows:

The perfluoromonoamidines were obtained by reaction of the corresponding perfluoronitriles with liquid ammonium at −60−−40° C.:

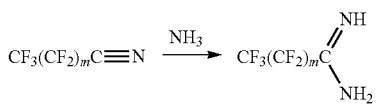

The perfluoromononitriles are made from the corresponding perfluoroacids as follows:

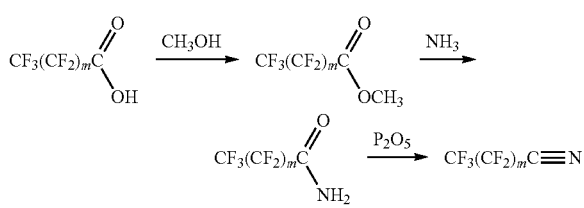

The perfluorodinitriles are made from corresponding perfluoroacids and perfluoroesters as follows:

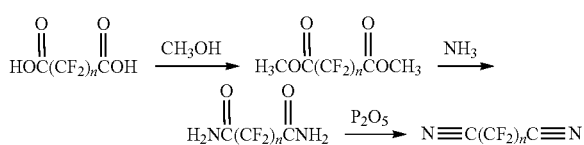

The perfluoroimidoylamidines of the invention are particularly useful as curing/vulcanizing agents for fluoroelastomeric compositions and more in particular for perfluoroelastomers. Accordingly, the invention also provides compositions containing perfluoroelastomers and the perfluoroimidoylamidines of the invention.

Within the present specification, a perfluoroelastomer may be any cured elastomeric material, derived by curing a perfluoroelastomeric composition which includes a curable perfluoropolymer having a functional group that allows the composition to cure. A perfluoroelastomer is substantially completely fluorinated with respect to the carbon atoms of the perfluoropolymer. By this it is meant that, based on this disclosure, that some residual hydrogen may exist in the functional crosslinking group in some perfluoroelastomeric compositions. The perfluoropolymers, used in perfluoroelastomeric compositions to form perfluoroelastomers upon cure, are formed by polymerizing one or more perfluorinated monomers, one of which preferably has a perfluorinated monomer having a functional group to allow curing.

As defined herein, a perfluoroelastomeric composition is a polymeric composition including a curable perfluoropolymer. The perfluoropolymer as noted above is formed by polymerizing two or more perfluorinated monomers, plus at least one perfluorinated monomer which has at least one functional group to permit curing, i.e. at least one perfluoropolymeric curesite monomer. Such materials are also referred to general as FFKMs (perfluoroelastomers) in accordance with the American Society for Testing and Materials (ASTM) definition (ASTM-D-1418-01a), incorporated herein fully by reference and are also described further herein. The definition provides that a perfluoroelastomer is a perfluorinated rubber of the polymethylene type having all fluoro, perfluoroalkyl, or perfluoroalkoxy substitutent groups on the polymer chain; a small fraction of these groups may contain functionality to facilitate curing/vulcanization. The perfluoroelastomer composition may include any suitable curable perfluoropolymer(s) (FFKM) capable of being cured to form a perfluoroelastomer, and one or more curing agents as described herein.

The perfluoroelastomer compositions preferably include two or more of various perfluorinated copolymers of at least one fluorine-containing ethylenically unsaturated monomer, such as tetrafluoroethylene (TFE); a perfluorinated olefin, such as hexafluoropropylene (HFP); and a perfluoroalkylvinyl ether (PAVE) which include alkyl groups that are straight or branched and which include one or more ether linkages, such as perfluoro(methyl vinyl ether), perfluoro (ethyl vinyl ether), perfluoro(propyl vinyl ether) and similar compounds. Examples of preferred PAVES include those described in U.S. Pat. No. 5,001,278 and in WO 00/08076, incorporated herein by reference. Other suitable PAVEs are described, for example, in U.S. Pat. Nos. 5,696,189 and 4,983,697, also incorporated herein by reference.

Preferred perfluoropolymers are terpolymers or tetrapolymers of TFE, PAVE, and at least one perfluorinated monomer which incorporates a functional group to permit curing and crosslinking of the terpolymer, at least one of said functional groups being capable of being cured by the curatives and co-curatives of the invention. In one embodiment, the monomer(s) containing the functional group provide sites which may be cured with either the inventive curative or inventive co-curatives or by other curatives not within the scope of the invention, but which are capable of having an accelerated cure when acted on by the curing agents of the present invention.

The most preferred monomers having the functional group capable of being cured include those having cyano groups, regardless of the location of the cyano group, e.g., primary and secondary cyano group containing monomers. Examples of cyano group containing monomers are described in detail herein, and may be found in, for example, U.S. Pat. No. 4,281,092. Such cyano group containing monomers are well known in the art. Combinations of one or more of these cyano group containing monomers with each other or with other well known functional group containing monomers may also be used within the scope of the invention.

Useful cyano group containing monomers include fluorinated olefins and fluorinated vinyl ethers, each having a cyano group of which the following are general examples: $CF_2=CF-O-(CF_2)_n-CN$, wherein n is from about 2 to about 12, and preferably about 2 to about 6; $CF_2=CF-O-(CF_2-CF(CF_3)-O)_n-CF_2-CF-(CF_3)-CN$, wherein n is from 0 to about 4, preferably from 0 to about 2; $CF_2=CF-[OCF_2CF(CF_3)]_m-(CF_2)_n-CN$, wherein m is from about 1 to about 2, and n is from about 1 to about 4; and $CF_2=CF-(CF_2)_n-O-CF(CF_3)-CN$, wherein n is from 2 to about 4.

Specific examples include primary functional group monomers such as $CF_2=CFOCF_2CF(CF_3)OCF_2CF_2CN$ (referred to generally as 8-CNVE) and secondary functional group monomers such as $CF_2=CF-O(CF_2)_3-O-CF(CF_3)-CN$. Such functional group containing monomers may be used alone or in combination. Especially preferred is a combination of functional group containing monomers as shown below in a fluoropolymeric or perfluoropolymeric chain as follows:

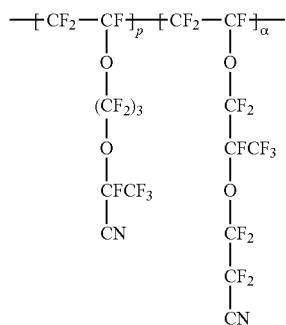

wherein p represents a secondary functional group containing monomer present in a fluoropolymer or perfluoropolymers in an amount from about 0.1 to about 12 mol %, preferably about 1 to about 4 mol %, and α represents a primary functional group containing monomer present in an amount from about 0.1 to about 12 mol % and preferably from about 1 to about 7 mol %. It is preferred that the molar ratio of the primary functional group containing monomer to the secondary functional group containing monomer in the copolymer is from about 1:1 to about 10:1, preferably 9:1.

It will be understood based on the present invention that additional types of functional group containing monomers which contain curable cyano groups and those which do not contain cyano groups may be used in addition to or, in certain cases, in place of the preferred functional group containing monomers noted above, provided that the functional group containing monomers are capable of being cured by the preferred curatives and co-curatives and/or capable of experiencing an accelerated curing reaction when using the curing agents of the invention as described herein. Common examples of other types of functional group containing monomers include olefins, including partially or fully halogenated olefins, such as ethylene, vinylidene fluoride, vinyl fluoride, trifluoroethylene, bromotetrafluorobutene, bromotrifluoroethylene, 1-hydropentafluoropropene and 2-hydropentafluoropropene. Such additional monomer(s) may be present in ranges as noted above and are preferably are generally present in amounts of about 0.1 to about 5 mole percent, more preferably about 0.1 to about 2.5 mole percent, and most preferably about 0.3 to about 1.5 mole percent.

Additional additives, such as co-curatives, curing agents or accelerators, other than those of the present invention; processing aids; fillers and the like may also be included as optional components of the perfluoroelastomeric compositions of the invention. Such additives include fillers such as graphite, carbon black, clay, silicon dioxide, fluoropolymeric particulates (for example, TFE homopolymer and copolymer micropowders), barium sulfate, silica, titanium dioxide, acid acceptors, cure accelerators, glass fibers, or polyaramid fibers such as Kevlar, other curing agents and/or plasticizers or other additives known or to be developed in the fluoroelastomeric art and perfluoroelastomeric art. Preferred perfluoropolymers/perfluoro-elastomers include SIMRIZ®™, available from Freudenberg of Germany, DYNEON®™, available from Minnesota Mining & Manufacturing in Minnesota, DAIEL-PERFLUOR®™, available from Daikin Industries, Ltd. of Osaka, Japan. Similar materials are also available from Ausimont S.p.A. in Italy and from Federal State Unitary Enterprise S.V. Lebedev Institute of Synthetic Rubber in Russia.

The preferred perfluoroelastomers for use with the invention are copolymers and terpolymers and tetrapolymers of TFE and perfluoroalkyl vinyl ethers with other perfluoro monomers containing cyano groups and having the following chemical structures:

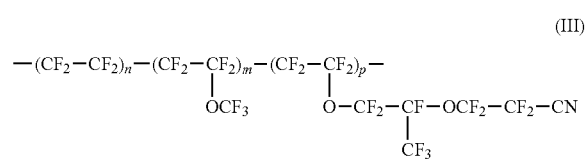

(III)

wherein m=30-70 mole %, n=20-55 mole % and p=0.1-10 mole % and more preferably wherein m=42-70 mole %, n=25-55 mole %, p=1-5 mole %;

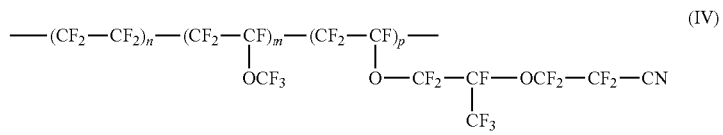

(IV)

wherein m=30-70 mole %, n=20-55 mole % and p=0.1-10 mole % and more preferably wherein m=42-70 mole %, n=25-55 mole %, p=1-5 mole %;

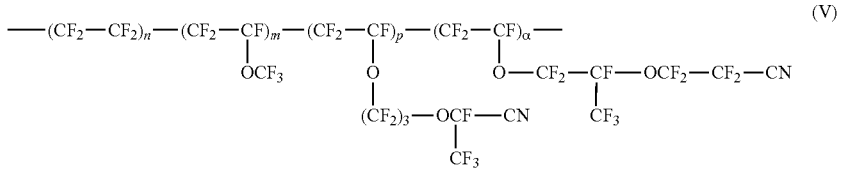

(V)

wherein m=30-70 mole %, n=20-55 mole %, p=0.1-8 mole %, and α=0.5-9 mole % and more preferably wherein m=42-70 mole %, n=25-55 mole %, p=1-4 mole %, a=1-7 mole %.

The above copolymers and terpolymers are made according to known procedures as further described for example in Russian Patent 2,137,781, and U.S. Pat. No. 4,281,092 incorporated in their entirety by reference.

Briefly, the perfluoroelastomers can be prepared by polymerization of appropriate monomer mixtures in the presence of a free radical generating initiator either in bulk, in solution in an inert solvent, in aqueous suspension, or in aqueous emulsion. Perfluoroelastomer polymerization techniques are also described in Logothetis, A. L. *Prog. Polym. Sci.* 1989, 14(2), 251-296. Such polymerizations are usually carried out in an aqueous medium by feeding monomers under pressure into a stirred reactor and initiating the polymerization with a persulfate initiator in the presence of a sulfite or bisulfite reducing agent, such as sodium sulfite. This type of initiation is referred to as redox initiation and results in production of polymer compositions having sulfonate endgroups. The Logothetis article further discloses that polymerization may be initiated by persulfates, such as ammonium or potassium persulfate, in the absence of a sulfite or bisulfite reducing agent. Thermally initiated free-radical polymerization using persulfates in the absence of a sulfite or bisulfite reducing agent results in the production of polymers having carboxylic acid endgroups which ionize to form carboxylate groups.

A preferred method of producing the perfluoroelastomer component of the present invention involves initiation of the copolymerization reaction with ammonium persulfate, in the absence of a sulfite or bisulfite reducing agent, in aqueous emulsion in a continuous well-stirred reactor with a residence time of 2-4 hours, at a temperature of 75° C.-90° C. and at a pressure of 2-8 MPa. Preferably the residence time is between 3.0-3.7 hours, the temperature is 80° C.-85° C., and the pressure is 6-8 MPa. Reducing agents include such compounds as sodium sulfite and sodium hydrogen sulfite. If levels of sulfite or bisulfite reducing agent above 5 mole percent, based on ammonium persulfate, are present, then the amount of sulfonate endgroups reaches a level which has detrimental effects on processability. In addition, in order to obtain the fast cure rates typical of the compositions of the present invention, the pH of the polymerization reaction is generally between 3.5-7.0, preferably between 4.5-6.5. Tetrafluoroethylene and perfluoro-(methylvinyl)ether are preferred monomers and are fed by compressor. Nitrile-containing monomer is preferably fed by liquid metering pump. This polymerization method results in production of a nitrile-containing copolymer having a plurality of nitrile groups or mixtures thereof.

The nitrile containing polymer, the curing agent and other additives can be mixed together by conventional means, such as a two-roll mill at 40° to 100° C. The mixed composition can be shaped and vulcanized by pressing into a mold and heating at 160° to 250° C., preferably 177° to 210° C., for 30-60 minutes. It is preferred to post cure the piece by heating it in an inert atmosphere, e.g. nitrogen, for a number of hours at a higher temperature.

The amount of curing/vulcanizing agent should be chosen to optimize the desired properties of the vulcanizate. In general, a slight excess of curing agent over the amount required to react with all the cure sites present in the polymer is used. Typically 0.5-5.0 parts by weight of the curative per 100 parts of polymer is required; the preferred range is 1.0-2.0 parts.

Fluoroelastomers which are cured according to this invention, they have excellent thermal and oxidative stability and better steam resistance as compared to the prior art compositions. In addition this invention permits the vulcanization of nitrile cure site fluoroelastomers without the use of organometallic compounds which may be undesirable in certain applications.

The cured compositions of the invention are also made by mixing the perfluoroelastomer in conventional mixers or on roll mills at the temperature of 20 to 25° C. Typically, the polymer is introduced into the mixer first and subsequently the curing agent is added.

The curing procedure is a two-staged process. In the first stage the formulation is heated, usually in a mold or other press form, at 150-200° C. for up to 45 minutes.

In the second stage, the formulation is heated stepwise from a temperature of 30° C. up to 300° C. for a period of 38-40 hours.

The resulting physical properties of the resulting cured perfluoroelastomers are evaluated using standard published test procedures:

Elastic and strength properties—GOST 270-75
Shore A Hardness—GOST 263-75
Compression Set at 2500, 3000, 330° C. for 24 hours at 20% compression—GOST 9.029-74.

Resistance to nitric acid was evaluated by the volume swelling coefficient after immersing in 60% $HNO_3$ at 80° C. for 70 hours.

In a further embodiment of the invention, 1 to 4 parts by weight of the perfluorodiimidoyl amidine (DPIA) curing agent is mixed with 100 parts by weight of copolymer based on TFE and perfluoroalkyl vinyl ethers.

The perfluorodiimidoyl amidines or tautomers thereof (DPIA) have the general structure:

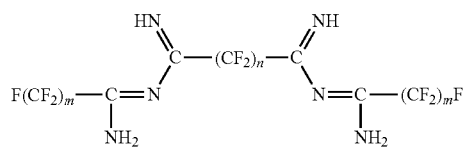

where n=2-8, m=2-8

The composition can also contain a co-curing agent (cure accelerator) and a filler.

As the accelerator one can add 1 to 4 parts by weight per 100 parts by weight of the copolymer of a mono-Perfluoroimidoyl amidine (PIA) of the general structure:

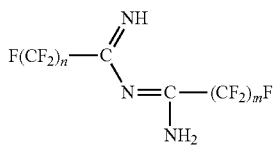

where n, m=2 to 8

As a filler one can add carbon black N990, or Aerosil R972, in a ratio 5 to 25 weight parts of the filler to 100 parts by weight of copolymer.

A further embodiment of the invention includes a curing composition comprising:

(a) 0.1% to 99.9% by weight of a compound of the formula I and tautomeric forms thereof:

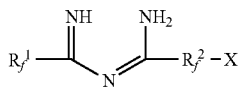
I wherein $R_f^1$ is selected from the group consisting of hydrogen, a straight chain, branched secondary or branched tertiary $C_1$-$C_{20}$ perfluoroalkyl group optionally containing ether or thioether linkages and $C_1$-$C_{10}$ perfluoroalicyclic group optionally containing ether or thioether groups; $R_f^2$ is a straight or branched $C_1$-$C_{20}$ perfluoroalkylene group optionally substituted with ether and thiother linkages; and X is selected from the group consisting of fluorine and

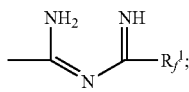

and (b) 0.1% to 99.9% by weight of a compound of the formula:

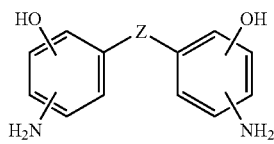

wherein Z is $SO_2$, O, CO, alkyl of 1-6 carbon atoms, perfluoroalkyl of 1-10 carbon atoms, or a carbon-carbon bond linking the two aromatic rings.

A more preferred composition for (a) and (b) above is 25% to 75% by weight of DPIA and 25% to 75% by weight of BOAP. The formulations are made by simply blending the two components together prior to adding to the perfluoroelastomer for curing purposes.

In another further embodiment, there is provided perfluoroelastomeric compositions cured with a composition comprising: (a) 0.1% to 99.9% by weight of a compound of the formula I and tautomeric forms thereof:

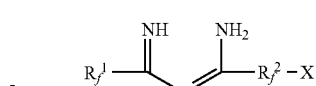
I wherein $R_f^1$ is selected from the group consisting of hydrogen, a straight chain, branched secondary or branched tertiary $C_1$-$C_{20}$ perfluoroalkyl group optionally containing ether or thioether linkages and $C_1$-$C_{10}$ perfluoroalicyclic group optionally containing ether or thioether groups; $R_f^2$ is a straight or branched $C_1$-$C_{20}$ perfluoroalkylene group optionally substituted with ether and thiother linkages; and X is selected from the group consisting of fluorine and

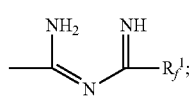

and (b) 0.1% to 99.9% by weight of a compound of the formula:

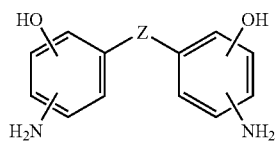

wherein Z is $SO_2$, O, CO, alkyl of 1-6 carbon atoms, perfluoroalkyl of 1-10 carbon atoms, or a carbon-carbon bond linking the two aromatic rings.

EXAMPLES

The present invention is illustrated by the following Examples, but should not be construed to be limited thereto. In the Examples, "part" and "%" are all part by weight or % by weight unless specified otherwise.

The following Examples are illustrative of the invention.

Example 1

Synthesis of perfluoro-$N^1$,$N^8$-diheptanimidoyloctanediimidamide (DPIA-65)

(i) Methyl Perfluoroheptanoate.

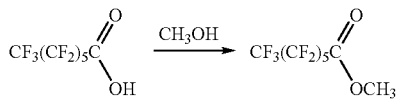

A 2-l, four-necked, round-bottomed flask equipped with stirrer, addition funnel, thermometer and reflux condenser, is charged with 728 g (2 mol) of dried perfluoroheptanoic acid, 160 g (5 mol) of methanol. The mixture is stirred and added dropwise 50 ml concentrated sulfuric acid and then heated to reflux for 4 hr. At the end of the reflux period the mixture is cooled to room temperature and poured into 2 l cold water. After separation of the phases, the lower organic phase is washed with water till pH neutral and dried over $CaCl_2$. Distillation of the crude gives 658 g (87%) of methyl perfluoroheptanoate, bp 139° C.

(ii) Perfluoroheptanoic Acid Amide.

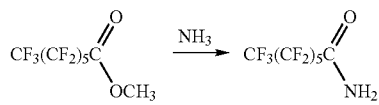

A 3-1, four-necked, round-bottomed flask equipped with stirrer, thermometer, reflux condenser with bubble counter and inlet gas-tube, is charged with 658 g (1.74 mol) of methyl perfluoroheptanoate and 1.5 l tetrahydrofurane. A stream of ammonia is passed from a pressure tank into the stirring solution. The ammonia feed rate is such that a negligible amount of gas is observed exiting the reactor as observed in the bubble counter. Temperature of the mixture increases to 40-50° C. Ammonium supply is continued until the temperature begins to decrease and an increasing volume of gas is observed exiting the reactor in the bubble counter. After ending the ammonia supply, the mixture is left to stand for 12 hr. Solvent is removed under reduced pressure, yielding 626 g p perfluoroheptanoic acid amide (99%), mp 127-128° C.

(iii) Perfluoroheptanenitrile.

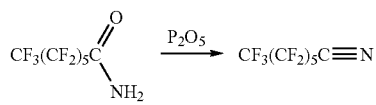

A 1-1, one-necked, round-bottomed flask is charged with 200 g (0.55 mol) of fine perfluoroheptanoic acid amide and 275 g $P_2O_5$. The flask is closed and the reactants are thoroughly mixed. The flask is then fitted with a condenser set downward and the mixture is heated to 250° C. The product is removed from the reaction mixture by direct distillation. The crude product is distilled with using a fractional distillation tube over a small quantity $P_2O_5$. The yield of perfluoroheptanenitrile is 152 g (80%), bp 74-75° C.

(iv) Perfluoroheptanamidine.

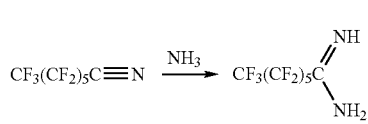

A 1-1, four-necked, round-bottomed flask is equipped with stirrer, thermometer, reflux condenser with drying tube (charged KOH) and inlet gas-tube. Ammonia is condensed in the flask by cooling in a mixture of dry ice and ethanol. When the volume of liquid ammonia reaches about 200 ml, the inlet gas-tube is removed and replaced with an addition funnel. Perfluoroheptanenitrile (152 g, 0.44 mol) is added dropwise. The reaction temperature is maintained at or below −55° C. at all times. Stirring is continued about 30 min, then the cooling bath is removed and mixture is left at room temperature to slowly evaporate excess $NH_3$. After evaporating the main part of $NH_3$, a water aspirator is attached to remove the remaining $NH_3$. The yield of perfluoroheptanamidine is 158 g (99%), mp −77-−76° C.

(v) Perfluorooctanedinitrile (Dinitrile Perfluorosuberic Acid).

Perfluorooctanedinitrile was obtained as described above for mononitrile, using double quantity of reagents for 1 mol input perfluorosuberic acid in the procedures 1-3. Same yields of perfluorooctanedinitrile and intermediates are obtained.

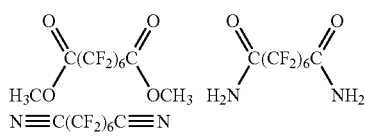

(vi) Perfluoro-$N^1$,$N^8$-diheptanimidoyloctanediimidamide.

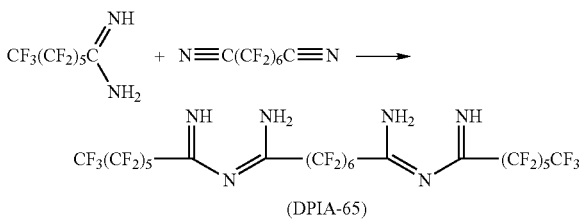

(DPIA-65)

A 1-1, four-necked, round-bottomed flask equipped with stirrer, addition funnel, thermometer and reflux condenser, is charged with 158 g (0.44 mol) of perfluoroheptanamidine, 300 ml of anhydrous ether and 77.4 g (0.22 mol) of perfluorooctanedinitrile was added in drops at a rate to maintain the internal temperature below 30° C. After the addition is complete, the reaction mixture is stirred for another 2 hr. After removal of the solvent under reduced pressure, product (235 g, (99.9%)) is obtained as a white solid, mp 92-93° C.

Example 2

Synthesis of perfluoro-$N^1$,$N^7$-dioctanimidoylheptanediimidamide (DPIA-56)

(i) Methyl Perfluorooctanoate.

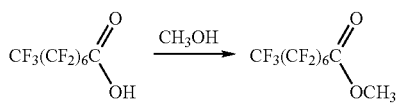

A 2-1, four-necked, round-bottomed flask equipped with stirrer, addition funnel, thermometer and reflux condenser, is charged with 828 g (2 mol) of dried perfluorooctanoic acid, 160 g (5 mol) of methanol. The mixture is stirred and 50 ml concentrated sulfuric acid is added dropwise. Then the mixture is heated to reflux for 4 hr. At the end of the reflux period the mixture is cooled to room temperature and poured into 2 l cold water. After separation of the phases, the lower organic phase is washed with water till pH neutral and dried over $CaCl_2$. Distillation of the crude gives 762 g (89%) of methyl perfluorooctanoate, bp 160° C.

(ii) Perfluoroheptanoic Acid Amide.

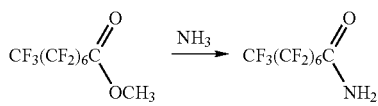

A 3-l, four-necked, round-bottomed flask equipped with stirrer, thermometer, reflux condenser with bubble counter and inlet gas-tube, is charged with 745 g (1.74 mol) of methyl perfluorooctanoate and 1.5 l tetrahydrofurane. A stream of ammonia is passed from a pressure tank into the stirring solution. The ammonia feed rate is such that a negligible amount of gas is observed exiting the reactor as observed in the bubble counter. Temperature of the mixture increases to 40-50° C. Ammonium supply is continued until the temperature begins to decrease and an increasing volume of gas is observed exiting the reactor in the bubble counter . . . . After ending of ammonium supply, the mixture is left to stand for 12 hr. Solvent is removed under reduced pressure, yielding 712 g p perfluorooctanoic acid amide (99%), mp 136-137° C.

(iii) Perfluorooctanenitrile.

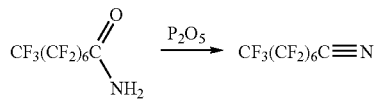

A 1-1, one-necked, round-bottomed flask is charged with 227 g (0.55 mol) of fine perfluorooctanoic acid amide and 275 g $P_2O_5$. The flask is closed and thoroughly mixed reagents. The flask is then fitted with a condenser set downward and heated mixture at 250° C. along with the product removed from the reaction mixture by direct distillation. The crude product is distilled using a fractional distillation tube over a small quantity $P_2O_5$. The yield of perfluorooctanenitrile is 174 g (80%), bp 92-93° C.

(iv) Perfluorooctanamidine.

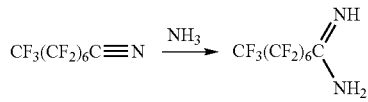

A 1-1, four-necked, round-bottomed flask is equipped with stirrer, thermometer, reflux condenser with drying tube (charged KOH) and inlet gas-tube Ammonia is condensed into the flask by cooling in a mixture of dry ice and ethanol. When the volume of liquid ammonium reaches about 200 ml, the inlet gas-tube is removed and replaced with an addition funnel. Perfluorooctanenitrile (174 g, 0.44 mol) is added dropwise. The reaction temperature is maintained at or below −55° C. at all times. Stirring is continued about 30 min, then the cooling bath is removed and mixture is left at room temperature to slowly evaporate excess $NH_3$. After evaporating the main part of $NH_3$, a water aspirator is attached to remove the remaining $NH_3$. The yield of perfluorooctanamidine is 181 g (99%), mp −61−−60° C.

(v) Perfluoroheptanedinitrile (Dinitrile Perfluoroheptanoic Acid).

Perfluoroheptanedinitrile was obtained as described above for mononitrile, used double quantity of reagents for 1 mol input perfluoroheptanoic acid in the procedures 1-3. Same yields of perfluoroheptanedinitrile and intermediates are obtained.

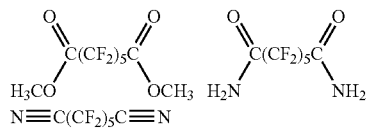

(vi) Perfluoro-$N^1$,$N^7$-dioctanimidoylheptanediimidamide.

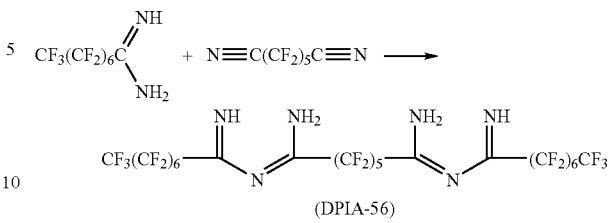

A 1-1, four-necked, round-bottomed flask equipped with stirrer, addition funnel, thermometer and reflux condenser, is charged with 181 g (0.44 mol) of perfluorooctanamidine, 300 ml of anhydrous ether and 66.4 g (0.22 mol) perfluoroheptanedinitrile was added in drops at a rate to maintain the internal temperature below 30° C. After the addition is complete, the reaction mixture is stirred for another 2 hr. After removal of the solvent under reduced pressure, product (247 g, (99.9%)) is obtained as a white solid, mp 95-96° C.

Example 3

Using the same chemistry as in examples 1 and 2 the following additional perfluoroimidoylamidines are synthesized:

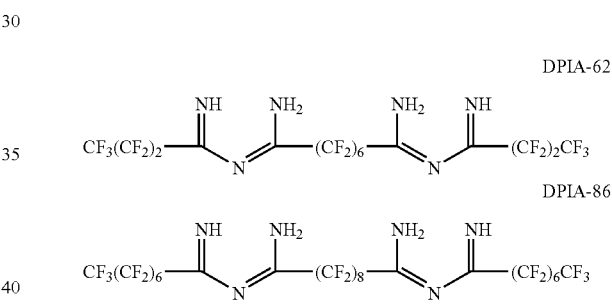

Example 4

Rubber samples for testing were made by the same general proceduce. Mixing is done on a roll mill at T=25° C., using 100 parts by weight of copolymer (V), where n=42 mole %, m=54.2 mole %, p=1 mole %, α=2.8 mole % and various weight parts of different DPIA samples—as indicated in Table 1 Mixing was carried out for 10 mins on the mill. Also included in Table 1 are samples made with different types of DPIA and co-curing agents PIA. For comparison tests (9-12) were made with various amounts of 4,4'-[2,2,2-trifluoro-1-(trifluoromethyl)-ethylidene]bis(2-aminophenol), which is referred to as BOAP in Table 1 and in subsequent examples.

The rubber blend is cured in a press mold for 30 minutes at 180° C., then in an oven for 38 hours, starting at a temperature of 25° C. and finishing at a temperature of 260° C. during the last 14 to 20 hours of the second stage of the curing process.

The present invention compositions (examples 1 to 8) and comparative examples of analogs (examples 9 to 12) are shown in Table 1. Test results are shown in Table 2 and Table 3. Vulcanized compositions without carbon black are transparent, while vulcanized compositions with carbon black are black.

TABLE 1

Content of composition

| Composition | Sample # 1 | 2 | 3 | 4 | 5 | 6 | 7 | 8 | Comparative examples 9 | 10 | 11 | 12 |
|---|---|---|---|---|---|---|---|---|---|---|---|---|
| Copolymer, weight parts | 100 | 100 | 100 | 100 | 100 | 100 | 100 | 100 | 100 | 100 | 100 | 100 |
| Composition of copolymer, Mole % | (V) n = 42 m = 54.2 p = 1 a = 2.8 | (V) n = 50 m = 42 p = 1 a = 7 | (IV) n = 68 m = 30 p = 2 | (III) n = 62 m = 36.8 p = 1.2 | (V) n = 70 m = 25 p = 4 a = 1 | (IV) n = 60 m = 35 p = 5 | (V) n = 42 m = 53 p = 4 a = 1 | (III) n = 42 m = 55 p = 3 | (V) n = 70 m = 25 p = 4 a = 1 | (V) n = 42 m = 54.2 p = 1 a = 2.8 | (V) n = 70 m = 25 p = 4 a = 1 | (V) n = 50 m = 42 p = 1 a = 7 |
| Curing agent, DPIA, weight parts | 3 | 1 | 4 | 3 | 2 | 2 | 4 | — | — | — | — | — |
| Content of DPIA, weight parts | n = 6 m = 6 | n = 8 m = 2 | n = 7 m = 3 | n = 6 m = 6 | n = 2 m = 8 | n = 6 m = 6 | n = 6 m = 4 | n = 3 m = 7 | — | — | — | — |
| Curing agent, BOAP, weight parts | — | — | — | — | — | — | — | — | 3 | 1 | 4 | 2 |
| Coagent of curing | — | — | — | 2 | 4 | — | — | — | — | — | — | — |
| Content PIA, weight parts | — | — | — | n = 8 m = 2 | n = 6 m = 6 | — | n = 2 m = 8 | — | — | — | — | — |
| Carbon Black N990 | — | — | — | — | 15 | 20 | 25 | — | — | — | 25 | — |
| Aerosil R972, weight parts | — | — | — | — | — | — | — | 5 | — | — | — | 5 |

TABLE 2

Physical and mechanical properties of vulcanized perfluorelastomers

| Property | Sample # 1 | 2 | 3 | 4 | 5 | 6 | 7 | 8 | 9 | 10 | 11 | 12 |
|---|---|---|---|---|---|---|---|---|---|---|---|---|
| Modulus 100% elongation, MPa | 2.7 | 2.2 | 3.1 | 2.9 | 10.1 | 10.3 | 10.6 | 6.6 | 2.1 | 1.9 | 10.1 | 6.1 |
| Tensile Stength, MPa | 12.1 | 13.0 | 12.0 | 12.3 | 17.1 | 18.35 | 18.49 | 15.2 | 10.1 | 9.8 | 18.1 | 15.0 |
| Relative elongation, % | 310 | 380 | 320 | 310 | 270 | 250 | 220 | 270 | 195 | 210 | 140 | 180 |
| Shore A Hardness | 73 | 60 | 63 | 71 | 82 | 80 | 82 | 85 | 73 | 71 | 86 | 80 |
| Resistance to HNO$_3$, (60% at 80 C. for 70 hours) | 0.12 | 0.13 | 0.2 | 0.15 | 0.12 | 0.13 | 0.14 | 0.12 | 0.75 | 0.55 | 0.70 | 0.65 |

TABLE 3

Compression Set (20% compression for 24 hours)

| Temperature, °C. | Sample # 1 | 2 | 3 | 4 | 5 | 6 | 7 | 8 | 9 | 10 | 11 | 12 |
|---|---|---|---|---|---|---|---|---|---|---|---|---|
| 300 | 10 | 9 | 9 | 8 | 13 | 15 | 15 | 12 | 26 | 31 | 51 | 45 |
| 330 | 22 | 23 | 21 | 22 | 29 | 30 | 33 | 27 | 49 | 66 | 92 | 81 |

As shown in the Tables 1, 2 and 3 the compositions of the present invention give vulcanizates having better compression set and increased stability to strong nitric acid for both the filled perfluoroelastomer blends and the unfilled perfluoroelastomer blends as well. The unfilled samples have light color.

Example 5

Several perfluoroelastomeric compositions are made according to Example 4 and their formulations and properties after curing with the curing agents of the invention are summarized I Table 4.

TABLE 4

Characteristics of rubber mixture and vulcanizates

| | Experimental number 1 | 2 | 3 | 4 | 5 | 6 | 7 | 8 | 9 | 10 |
|---|---|---|---|---|---|---|---|---|---|---|
| Mooney's viscosity of gum | 140 | 140 | 140 | 140 | 140 | 140 | 140 | 140 | 140 | 140 |
| Composition of the blend, weight parts | | | | | | | | | | |
| PFK (perfluoroelastomer gum) | 100.0 | 100.0 | 100.0 | 100.0 | 100.0 | 100.0 | 100.0 | 100.0 | 100.0 | 100.0 |
| BOAP | 0.5 | 1.0 | 1.5 | 2.0 | 3.0 | | | | | |
| DPIA-56 | | | | | | 2.0 | | | | |
| DPIA-65 | | | | | | | 1.0 | 2.0 | 3.0 | 4.0 |
| DPIA-62 | | | | | | | | | | |
| DPIA-86 | | | | | | | | | | |

TABLE 4-continued

Characteristics of rubber mixture and vulcanizates

Rheometric data ("Monsanto" 100S, T = 177° C.)

| | | | | | | | | | | |
|---|---|---|---|---|---|---|---|---|---|---|
| $t_s$, min | | 6.00 | 5.50 | 5.50 | 5.40 | 5.50 | 2.20 | 1.70 | 2.00 | 1.30 | 1.30 |
| $t_{50}$, min | | 28.80 | 28.00 | 30.80 | 29.50 | 35.00 | 3.50 | 3.30 | 3.00 | 2.50 | 2.80 |
| $t_{90}$, min | | 57.50 | 66.00 | 66.00 | 67.80 | 75.30 | 11.00 | 19.00 | 10.50 | 25.00 | 7.30 |
| $R_v$, min$^{-1}$ | | 1.94 | 1.65 | 1.65 | 1.60 | 1.43 | 12.00 | 5.85 | 11.70 | 4.21 | 16.70 |
| $M_L$, Nm | | 0.80 | 0.77 | 0.77 | 0.79 | 0.68 | 1.30 | 1.28 | 1.28 | 1.33 | 0.89 |
| $M_{HF}$, Nm | | 3.50 | 3.93 | 3.93 | 3.57 | 3.95 | 3.20 | 2.94 | 3.09 | 3.36 | 3.95 |

Physical and mechanical characteristics

| | | | | | | | | | | |
|---|---|---|---|---|---|---|---|---|---|---|
| Modulus at 100% elongation, MPa | | 1.7 | 1.7-1.9 | 1.9 | 2.1 | 2.3 | 2.0 | 2.0 | 2.0 | 1.9 | 2.1 |
| Tensile strength, MPa | | 6.6 | 5.2-7.9 | 6.5 | 11.2 | 12.0 | 11.0 | 9.8 | 10.2 | 10.5 | 8.8 |
| Relative elongation at break, % | | 290 | 260-290 | 280 | 280 | 250 | 300 | 310 | 310 | 300 | 290 |
| Hardness | | 68 | 65 | 67 | 69 | 74 | 65 | 62 | 62 | 64 | 67 |
| Compression set, % | 250° C. | 59 | 43 | 37 | 33 | — | 24 | 54 | 22 | 17 | — |
| (20% compression, 24 h) | 330° C. | 74 | 66 | 61 | 58 | 74 | — | 65 | 25 | 51 | — |

| | | Experimental number | | | | | | | | |
|---|---|---|---|---|---|---|---|---|---|---|
| | | 11 | 12 | 13 | 14 | 15 | 15 | 17 | 18 | 19 |
| | Mooney's viscosity of gum | 140 | 140 | 140 | 140 | 140 | 130 | 130 | 115 | 115 |

Composition of the blend, weight parts

| | | | | | | | | | |
|---|---|---|---|---|---|---|---|---|---|
| PFK (perfluoroelastomer gum) | | 100.0 | 100.0 | 100.0 | 100.0 | 100.0 | 100.0 | 100.0 | 100.0 | 100.0 |
| BOAP | | | | | | | 2.0 | | 1.0 | |
| DPIA-56 | | | | | | | | | | |
| DPIA-65 | | | | | | | | 3.0 | | 2.0 |
| DPIA-62 | | 1.0 | 2.0 | 3.0 | 4.0 | | | | | |
| DPIA-86 | | | | | | 2.0 | | | | |

Rheometric data ("Monsanto" 100S, T = 177° C.)

| | | | | | | | | | |
|---|---|---|---|---|---|---|---|---|---|
| $t_s$, min | | 1.80 | 1.10 | 1.10 | 1.30 | 1.30 | 5.30 | 1.70 | 5.50 | 1.30 |
| $t_{50}$, min | | 3.70 | 2.30 | 2.30 | 7.00 | 2.70 | 30.50 | 3.80 | 30.50 | 2.50 |
| $t_{90}$, min | | 32.00 | 28.60 | 16.00 | 58.00 | 9.50 | 71.30 | 49.00 | 63.00 | 14.8 |
| $R_v$, min$^{-1}$ | | 3.30 | 3.64 | 6.70 | 1.76 | 12.20 | 1.51 | 2.11 | 1.74 | 7.40 |
| $M_L$, Nm | | 1.18 | 1.49 | 1.62 | 1.74 | 1.15 | 0.47 | 1.03 | 0.55 | 1.27 |
| $M_{HF}$, Nm | | 2.66 | 3.58 | 3.56 | 3.05 | 2.91 | 3.19 | 3.05 | 4.00 | 3.33 |

Physical and mechanical characteristics

| | | | | | | | | | | |
|---|---|---|---|---|---|---|---|---|---|---|
| Modulus at 100% elongation, MPa | | 1.8 | 3.1 | 2.7 | 1.7 | 2.0 | 1.9 | 1.8 | 1.4 | 1.4 |
| Tensile strength, MPa | | 8.4 | 9.1 | 8.0 | 9-10 | 8.7 | 6.1 | 6.4 | 7.1 | 6.6 |
| Relative elongation at break, % | | 310 | 240 | 240 | 290 | 330 | 260 | 353 | 340 | 380 |
| Hardness | | 65 | 73-69 | 63-68 | 68 | 67 | 70 | 64 | 60 | 56 |
| Compression set, % | 250° C. | — | 21 | 18 | 22 | 58 | 23 | 23-27 | 46 | 27 |
| (20% compression, 24 h) | 330° C. | — | — | 21 | — | — | — | 48 | — | 56 |

Example 6

Several perfluoroelastomeric compositions are made according to Example 4. The perfluoroelastomer gum used in this example is FluorStar® PFK-65, a commercial perfluoroelastomer gum available from Lodestar, Inc. 8 Arbor Dr. Howell, N.J. Their formulations and properties after curing with the curing agent of Example 1 (DPIA-65) of the invention and compared to formulations containing BOAP, as well as both curing agents (DPIA-65 and BOAP together) are summarized in Table 5.

TABLE 5

Characteristics of vulcanizates made with DPIA-65, BOAP and mixtures of DPIA-65 and BOAP

| | Experimental lots | | | | |
|---|---|---|---|---|---|
| | 1 | 2 | 3 | 4 | 5 |

Composition of the blend, weight parts

| | | | | | |
|---|---|---|---|---|---|
| PFK-65 (perfluoroelastomer gum) | 100 | 100 | 100 | 100 | 100 |
| BOAP | 1.0 | — | 1.0 | — | 1.0 |
| DPIA-65 | — | 2.0 | 1.0 | 2.0 | 1.0 |

Rheometric data ("Monsanto" 100S)

| | | | | | |
|---|---|---|---|---|---|
| Test temperature, ° C. | 177 | 177 | 177 | 160 | 160 |
| $t_s$, min | 6.7 | 1.8 | 2.6 | 1.7 | 3.3 |
| $t_{50}$, min | 26.8 | 4.0 | 10.9 | 5.3 | 24.6 |
| $t_{90}$, min | 57.0 | 27.0 | 27.5 | 31.3 | 61.5 |
| $R_v$, min$^{-1}$ | 1.99 | 3.97 | 4.02 | 3.38 | 1.72 |
| $M_L$, Nm | 0.36 | 0.73 | 0.48 | 0.71 | 0.62 |
| $M_{HF}$, Nm | 3.69 | 2.88 | 3.71 | 3.01 | 3.74 |

Physical and mechanical characteristics

| | | | | | |
|---|---|---|---|---|---|
| Rebound elasticity | 58 | 56 | 57 | — | — |
| Hardness | 4 | 4 | 4 | — | — |
| Compression 250° C. | 25 | 19 | 19 | | |

TABLE 5-continued

Characteristics of vulcanizates made with DPIA-65, BOAP and mixtures of DPIA-65 and BOAP

| | Experimental lots | | | | |
|---|---|---|---|---|---|
| | 1 | 2 | 3 | 4 | 5 |
| set, % (20% 300° C. compression, 24 h) | 27 | 26 | 22 | — | — |

The data from table 5 shows that curing agent DPIA-65 shows faster curing rate as compared to BOAP. Especially it is observed for the rheometric parameter $t_S$. In case of mixture BOAP and DPIA-65 (1:1, experiment #3), the rheometric characteristics have intermediate values. The physical and mechanical characteristics of the samples are similar but the samples made with DPIA and particularly the binary mixture of DPIA and BOAP have better compression set, especially at 300° C.

Example 7

Several perfluoroelastomeric compositions are made according to Example 4 and their formulations and properties after curing with the curing agent the invention and compared to BOAP are summarized in Table 6. The perfluoroelastomer gum used in this example is Fluor Star® PFK-65, a commercial perfluoroelastomer gum available from Lodestar, Inc. 8 Arbor Dr. Howell, N.J.

TABLE 6

Properties of the rubber blends and vulcanizates based on PFK-65 with different curing agents

| | Sample # | | | |
|---|---|---|---|---|
| Parameter | 16 | 2 g | 63/1K | 63/3 g |
| Composition of rubber blend, weight parts | | | | |
| Gum | 100.0 | 100.0 | 100.0 | 100.0 |
| BOAP | 1.0 | — | 1.0 | — |
| DPIA | — | 2.0 | — | 2.0 |
| Carbon black N-990 | — | — | 25.0 | 25.0 |
| Rheometric properties, T = 177 C. | | | | |
| ts, min. | 4.5 | 1.3 | 4.0 | 0.9 |
| t50, min. | 17.7 | 3.2 | 16.7 | 3.3 |
| t90, min. | 41.0 | 31.0 | 37.3 | 21.0 |
| Rv, min$^{-1}$ | 2.73 | 3.3 | 3.0 | 4.97 |
| Mz, H m | 0.68 | 0.95 | 0.38 | 0.64 |
| M$_{HF}$, H m | 4.69 | 3.81 | 5.0 | 4.2 |
| Physical and mechanical properties | | | | |
| Curing conditions | 30 min at 177° C. | 20 min. at 160° C. | 30 min. at 177° C. | |
| Modulus 100%, MPa | 1.7 | 1.1 | 6.1 | 5.6 |
| Tensile Strength, MPa | 11.0 | 7.4 | 18.0 | 13.4 |
| Relative Elongation, % | 230 | 220 | 180 | 220 |
| Residual Elongation, % | 2 | 2 | 2 | 2 |
| Shore A Hardness | 65 | 56 | 76 | 75 |
| Elasticity at rebound at 23° C. | 7 | 4 | 4 | 4 |
| at 100° C. | 56 | 51 | 41 | 45 |
| Compression Set: 20% Compression for 24 hours, % at | | | | |
| 250° C. | 15 | 13 | 41 | 28 |
| 300° C. | 18 | — | 48 | 29 |
| 330° C. | Destr. | — | 52 | 31 |

TABLE 6-continued

Properties of the rubber blends and vulcanizates based on PFK-65 with different curing agents

| | Sample # | | | |
|---|---|---|---|---|
| Parameter | 16 | 2 g | 63/1K | 63/3 g |
| Heat aging 300° C. for 70 hours | | | | |
| Modulus 100%, MPa | 1.3 | 1.1 | 2.6 | 2.0 |
| Tensile Strength, MPa | 7.1 | 9.6 | 11.6 | 6.3 |
| Relative Elongation, % | 240 | 215 | 220 | 260 |
| Residual Elongation, % | 2 | 2 | 6 | 12 |
| Shore A Hardness | 59 | 57 | 69 | 72 |
| Compression Set: 20% | 24 | 22 | 45 | 31 |
| Compression 300° C. for 70 hours, % | | | | |

The curing agents of the present invention i.e., DPIA, have many advantages over BOAP of the prior art:

(1) DPIA melts at a lower temperature than BOAP. Since DPIA liquefies below the temperature used to process the perfluoroelastomer mixture, more uniform dispersions into the perfluoroelastomer is achieved. The melting point of BOAP is above the temperature used to process the perfluoroelastomer.

(2) The curing agents of the invention have faster cure rate as demonstrated by the rheometric data.

(3) Lower temperatures are required for the vulcanization process.

(4) The curing agents of the invention give a perfluoroelastomeric product having lighter color.

(5) The resulting product has lower hardness and higher elongation.

(6) The resulting product has lower compression set at 250° C. and above.

(7) The resulting product has similar modulus and tensile strength.

While the many forms of the invention herein disclosed constitute presently preferred embodiments, many others are possible and further details of the preferred embodiments and other possible embodiments are not to be construed as limitations. It is understood that the terms used herein are merely descriptive rather than limiting and that various changes and many equivalents may be made without departing from the spirit or scope of the claimed invention.

What is being claimed is:

1. A composition consisting of:

(a) a fluorocarbon polymer selected from the group consisting of:

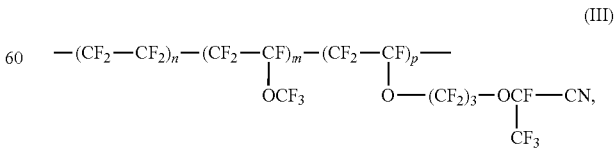

(III)

wherein m=42-70 mol %, n=25-55 mol %, and p=1-5 mol %;

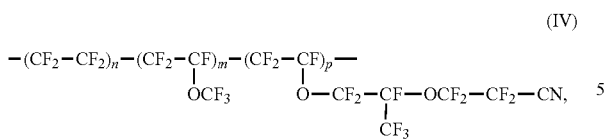
(IV)

wherein m=42-70 mol %, n=25-55 mol %, and p=1-5 mol %; and

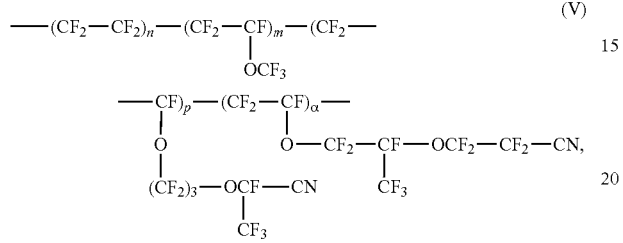
(V)

wherein m=42-70 mol %, n=25-55 mol %, p=1-4 mol %, and α=1-7 mol %; and (b) a curing agent selected from the group consisting of

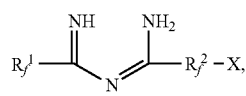
(I)

wherein $R_f^1$ is selected from the group consisting of straight chain, branched secondary or branched tertiary $C_1$-$C_6$ and $C_8$-$C_{20}$ perfluoroalkyl groups optionally containing ether or thioether linkages and $C_1$-$C_{10}$ perfluoroalicyclic groups optionally containing ether or thioether groups; $R_f^2$ is a straight or branched $C_4$-$C_6$ and $C_8$-$C_{20}$ perfluoroalkylene group optionally substituted with ether and thioether linkages; and X is

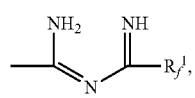

wherein $R_f^1$ is as defined above; and

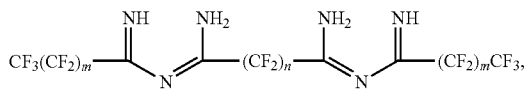

wherein n=4, 5, 7, or 8, and m=0, 1, 2, 3, 4, 5, or 7.

2. A curable perfluoroelastomer composition consisting of:

(a) a perfluoroelastomer selected from the group consisting of:

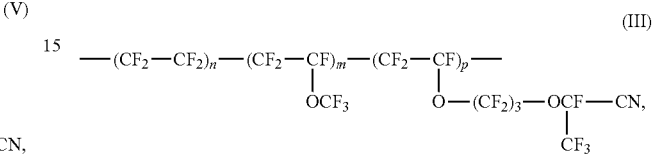
(III)

wherein m=42-70 mol %, n=25-55 mol %, and p=1-5 mol %;

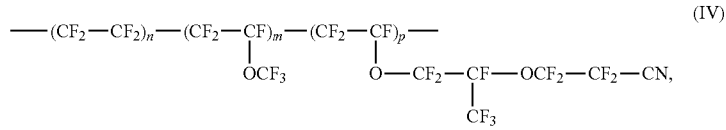
(IV)

wherein m=42-70 mol %, n=25-55 mol %, and p=1-5 mol %; and

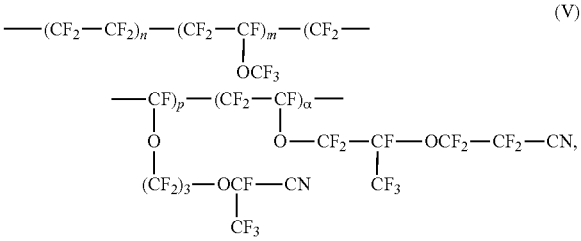
(V)

wherein m=42-70 mol %, n=25-55 mol %, p=1-4 mol %, and α=1-7 mol %; and (b) about 0.1 to about 10 parts by weight per hundred parts by weight perfluoroelastomer of a fluorinated imidoylamidine curing agent having the formula:

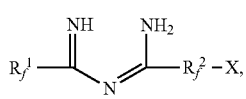
(I)

wherein $R_f^1$ is selected from the group consisting of straight chain, branched secondary or branched tertiary $C_1$-$C_6$ and $C_8$-$C_{20}$ perfluoroalkyl groups optionally containing ether or thioether linkages and $C_1$-$C_{10}$ perfluoroalicyclic groups optionally containing ether or thioether groups; $R_f^2$ is a straight or branched $C_4$-$C_6$ and $C_8$-$C_{20}$ perfluoroalkylene group optionally substituted with ether and thioether linkages; and X is

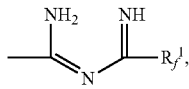

wherein $R_f^1$ is as defined above; and
optionally, a co-curing agent compound and tautomeric forms thereof having the formula:

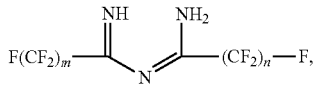

wherein n=1, 2, 3, 4, 5, 6, or 8, and m=0-6.

3. The composition of claim 2, wherein $R_f^1$ is a straight chain $C_1$-$C_6$ and $C_8$ perfluoroalkyl group and $R_f^2$ is a straight chain $C_4$-$C_6$ and $C_8$ perfluoroalkylene group.

4. The composition of claim 2, wherein $R_f^1$ is a straight chain $C_5$-$C_6$ perfluoroalkyl group and $R_f^2$ is a straight chain $C_5$-$C_6$ and $C_8$ perfluoroalkylene group.

5. The composition of claim 2, wherein the fluorinated imidoylamidine compound and tautomeric forms thereof have the formula:

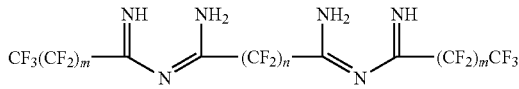

wherein n=4, 5, 7, or 8, and m=0, 1, 2, 3, 4, 5, or 7.

6. The composition of claim 5, wherein n=5, 7, or 8, and m=5.

7. A curing composition consisting of:
(a) 0.1% to 99.9% by weight if a compound of the formula (I) and tautomeric forms thereof:

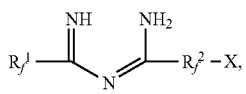

wherein $R_f^1$ is selected from the group consisting of straight chain, branched secondary or branched tertiary $C_1$-$C_6$ and $C_8$-$C_{20}$ perfluoroalkyl groups optionally containing ether or thioether linkages and $C_1$-$C_{10}$ perfluoroalicyclic groups optionally containing ether or thioether groups; $R_f^2$ is a straight or branched $C_4$-$C_6$ and $C_8$-$C_{20}$ perfluoroalkylene group optionally substituted with ether and thioether linkages; and X is selected from the group consisting of fluorine and

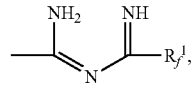

wherein $R_f^1$ is as defined above; and
(b) 0.1% to 99.9% by weight of a compound of the formula:

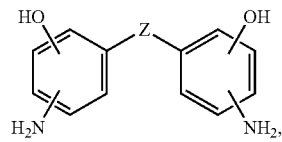

wherein Z is $SO_2$, O, CO, alkyl of 1-6 carbon atoms, perfluoroalkyl of 1-10 carbon atoms, or a carbon-carbon bond linking the two aromatic rings, wherein said curing composition is used to cure perfluoroelastomers selected from the group consisting of:

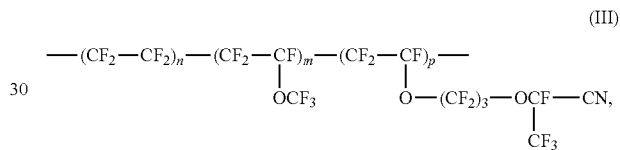

wherein m=42-70 mol %, n=25-55 mol %, and p=1-5 mol %;

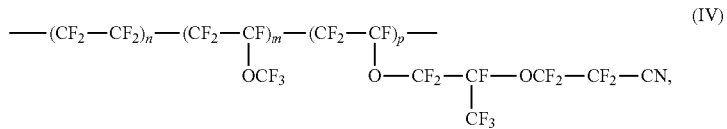

wherein m=42-70 mol %, n=25-55 mol %, and p=1-5 mol %; and

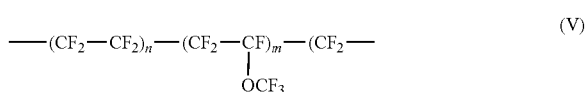

wherein m=42-70 mol %, n=25-55 mol %, p=1-4 mol %, and α=1-7 mol %.

8. The composition of claim 7, wherein said compound (a) is selected from the group consisting of: perfluoro-$N^1,N^8$-diheptan-imidoyloctanediimidamide and perfluoro-$N^1,N^7$-dioctanimidoylheptanediimidamide; and said (b) is selected from the group consisting of: (1) 4,4'-[2,2,2-trifluoro-1-(trifluoromethyl)-ethylidene]-bis(2-aminophenol), (2) 4,4'-sulfonylbis(2-aminophenol), (3) 3,3'-diaminobenzidine, and (4) 3,3',4,4'-tetraminobenzophenone.

9. The composition of claim 7, wherein said compound (a) is perfluoro-$N^1,N^8$-diheptan-imidoyloctanediimidamide and said compound (b) is 4,4'-[2,2,2-trifluoro-1-(trifluoromethyl)-ethylidene]-bis(2-aminophenol).

10. The composition of claim 7, wherein said compound (a) is perfluoro-$N^1,N^7$-dioctanimidoylheptanediimidamide and said compound (b) is 4,4'-[2,2,2-trifluoro-1-(trifluoromethyl)-ethylidene]-bis(2-aminophenol).

11. A curable perfluoroelastomer composition consisting of:
(a) a perfluoroelastomer selected from the group consisting of:

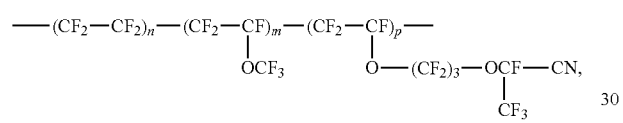

(III)

wherein m=42-70 mol %, n=25-55 mol %, and p=1-5 mol %;

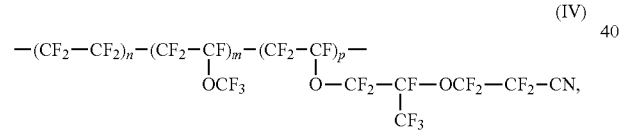

(IV)

wherein m=42-70 mol %, n=25-55 mol %, and p=1-5 mol %; and

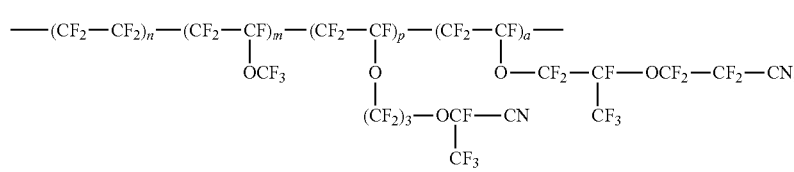

(V)

wherein m=42-70 mol %, n=25-55 mol %, p=1-4 mol %, and α=1-7 mol %; and (b) an effective amount of a curing composition consisting of:

(i) 0.1% to 99.9% by weight if a compound of the formula (I) and tautomeric forms thereof:

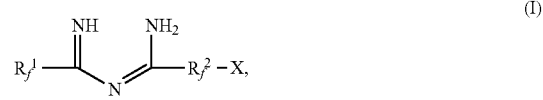

(I)

wherein $R_f^1$ is selected from the group consisting of straight chain, branched secondary or branched tertiary $C_1$-$C_6$ and $C_8$-$C_{20}$ perfluoroalkyl groups optionally containing ether or thioether linkages and $C_1$-$C_{10}$ perfluoroalicyclic groups optionally containing ether or thioether groups; $R_f^2$ is a straight or branched $C_4$-$C_6$ and $C_8$-$C_{20}$ perfluoroalkylene group optionally substituted with ether and thioether linkages; and X is

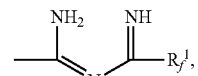

wherein $R_f^1$ is as defined above; and (ii) 0.1% to 99.9% by weight of a compound of the formula:

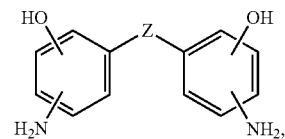

wherein Z is $SO_2$, O, CO, alkyl of 1-6 carbon atoms, perfluoroalkyl of 1-10 carbon atoms, or a carbon-carbon bond linking the two aromatic rings.

12. The perfluoroelastomeric composition of claim 11, wherein compound (i) is perfluoro-$N^1,N^8$-diheptan-imidoyloctanediimidamide and compound (ii) is 4,4'-[2,2,2-trifluoro-1-(trifluoromethyl)-ethylidene]-bis(2-aminophenol).

13. The perfluoroelastomeric composition of claim 11, wherein compound (i) is perfluoro-$N^1,N^7$-dioctanimidoylheptanediimidamide and compound (ii) is 4,4'-[2,2,2-trifluoro-1-(trifluoromethyl)-ethylidene]-bis(2-aminophenol).

* * * * *